US009375581B2

(12) United States Patent
Baru et al.

(10) Patent No.: US 9,375,581 B2
(45) Date of Patent: Jun. 28, 2016

(54) IMPLANTABLE STIMULATION DEVICE, STIMULATION SYSTEM AND METHOD FOR DATA COMMUNICATION

(71) Applicant: BIOTRONIK SE & CO. KG, Berlin (DE)

(72) Inventors: Marcelo Baru, Tualatin, OR (US); J. Christopher Moulder, Portland, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 58 days.

(21) Appl. No.: 14/176,027

(22) Filed: Feb. 7, 2014

(65) Prior Publication Data

US 2014/0222098 A1    Aug. 7, 2014

Related U.S. Application Data

(60) Provisional application No. 61/761,707, filed on Feb. 7, 2013, provisional application No. 61/906,902, filed on Nov. 21, 2013.

(51) Int. Cl.
*A61N 1/00* (2006.01)
*A61N 1/37* (2006.01)
(Continued)

(52) U.S. Cl.
CPC .............. *A61N 1/3708* (2013.01); *A61N 1/375* (2013.01); *A61N 1/37211* (2013.01); *A61N 1/37217* (2013.01); *A61N 1/37276* (2013.01)

(58) Field of Classification Search
CPC .................................................. A61N 1/36014
USPC ................................................ 607/16, 46, 57
See application file for complete search history.

(56) References Cited

U.S. PATENT DOCUMENTS 5,769,877 A    6/1998    Barreras
5,833,710 A    11/1998   Jacobson
(Continued)

FOREIGN PATENT DOCUMENTS

EP    2508226    10/2012
EP    2540340    1/2013

OTHER PUBLICATIONS

European Search Report issued for EP Appl. No. 14153926.2, dated Apr. 4, 2014, 8 pages.

*Primary Examiner* — Nicole F Lavert
*Assistant Examiner* — Nadia A Mahmood
(74) *Attorney, Agent, or Firm* — Arc IP Law, PC; Joseph J. Mayo

(57) ABSTRACT

An implantable stimulation device including a stimulation module and a data communication module. The stimulation device includes electrodes to delivery stimulation pulses, a voltage source, a DC-blocking capacitor and autoshort switch. The voltage source is connected to the electrodes via stimulation-pulse-switch(es) that controls delivery pacing pulses. The DC-blocking capacitor is connected with the voltage source and an electrode. The autoshort switch allows discharging of the DC-blocking capacitor via the electrodes when closed. The data communication module includes a data transmission control module connected to the autoshort switch and/or the at least one stimulation-pulse-switch, to alternatingly open and close the autoshort switch or the at least one stimulation-pulse-switch respectively, during an autoshort period following the delivery of a stimulation pulse or during a stimulation pulse period, respectively, to modulate an autoshort pulse or a stimulation pulse peak amplitude, respectively.

10 Claims, 8 Drawing Sheets

(51) Int. Cl.
*A61N 1/372* (2006.01)
*A61N 1/375* (2006.01)

(56) References Cited

U.S. PATENT DOCUMENTS

| | | | |
|---|---|---|---|
| 6,704,602 B2 | 3/2004 | Berg et al. | |
| 7,945,333 B2* | 5/2011 | Jacobson | A61N 1/3704 607/30 |
| 8,412,352 B2 | 4/2013 | Griswold et al. | |
| 2006/0122657 A1 | 6/2006 | Deal et al. | |
| 2010/0114248 A1 | 5/2010 | Donofrio et al. | |
| 2011/0190849 A1 | 8/2011 | Faltys et al. | |
| 2012/0078322 A1 | 3/2012 | Dal Molin et al. | |
| 2012/0109236 A1 | 5/2012 | Jacobson et al. | |
| 2012/0179218 A1 | 7/2012 | Moulder | |
| 2012/0259382 A1* | 10/2012 | Trier | A61N 1/36071 607/46 |

* cited by examiner

IMPLANTABLE STIMULATION DEVICE, STIMULATION SYSTEM AND METHOD FOR DATA COMMUNICATION

This application claims the benefit of U.S. Provisional Patent Application 61/761,707, filed on 7 Feb. 2013, and U.S. Provisional Patent Application 61/906,902, filed on 21 Nov. 2013, the specifications of which are hereby incorporated herein by reference.

BACKGROUND OF THE INVENTION

1. Field of the Invention

Embodiments of the invention generally relate to implantable medical devices and more particularly to communication techniques to transmit data from the implanted medical device to an external programmer.

2. Description of the Related Art

Typically, implantable medical devices, in particular implantable stimulation devices, such as implantable therapy and/or monitoring devices including pacemakers, cardioverters and defibrillators or the like, may include data communication means to transmit data from the implantable stimulation device to an external device, such as a device external to the body, or vice versa.

Generally, a system for data communication with an implantable stimulation device thus may include an implantable stimulation device and an external device such as a programmer.

A typical implantable stimulation device includes a battery, a monitoring and/or therapy control unit, and in some cases one or more therapy units such as stimulation modules, and a memory for storing control program and/or data sensed by the implantable stimulation device. If the implantable stimulation device is a pacemaker or an implantable cardioverter/defibrillator (ICD), generally, the therapy units include stimulation (pacing) units for generating and delivering electric stimulation pulses to a patient's heart tissue (myocardium). Often, sensing units for sensing cardiac activity are provided. Sensing units may often process electrical signals that represent electrical potentials that may be picked up via electrodes, e.g., in the heart.

In order to transmit data acquired by the implantable stimulation device to an external device or to other implanted devices, generally, a telemetry unit may be provided. Typically, the telemetry unit may allow a bidirectional data communication, that is, the telemetry unit may transmit and receive data wirelessly.

Limited battery capacity of an implantable stimulation device often calls for energy-efficient data communication. An implantable stimulation device with limited battery power typically requires a low-power communication scheme in order to program it and to download acquired data. With extremely low-power communication, generally, more data can be transmitted more often.

Typically, the implantable stimulation device must source all of the energy required for transmitting data in all of the communication solutions disclosed in prior art. Pulses generated for data transmission generally use either current or voltage to create an electric field that is sensed at the receiver. Thus, the receiver often passively decodes the communication and the transmitter often uses sufficient energy to enable the receiver to sense the signal. This arrangement is often detrimental to extremely low-power devices, such as intracardiac leadless pacemakers (iLP). The available energy for these devices is generally extremely limited making high-energy pulses problematic. Typically, the pulses for data transmission must generally be sub-threshold because clinical complications could occur if communication caused capturing of surrounding tissue, e.g. myocardium of the heart. To reduce the possibility of capturing the heart, generally, very short transmission windows must be used to limit communication during times when the heart is refractory to stimulation. These reduced communication times often precipitate the use of high-data transmission rates that subsequently require higher clock rates for the implantable device. The higher clock rates generally complicate design and increase power consumption.

Typical communication schemes utilize sub-threshold pulses to galvanically transmit data to another device. When supra-threshold pulses are used, generally, the data is encoded within the pulse itself. The information in either case is often transmitted by pulses that are received and decoded. Typically, the electric field generated by the pulses is detected at the receiver, where all of the energy required for transmission is generated at the transmitter.

United States Patent Publication 2012/0078322 to Molin et al., entitled "Apparatus And Methods For Wireless Communication Via Electrical Pulses Conducted By The Interstitial Tissue Of The Body For An Active Implantable Medical Device", discloses the use of biphasic pulses to maintain charge balancing while communicating.

U.S. Pat. No. 8,412,352 to Griswold et al., entitled "Communication Dipole For Implantable Medical Device", discloses a device where the fixation mechanism is also connected to the communications module. The module of Griswold et al. uses electric pulses to communicate with another device.

U.S. Pat. No. 7,945,333 to Jacobson, entitled "Programmer For Biostimulator System", discloses the combination of a programmer and an implantable device that communicate using encoded pulses. According to Jacobson, these pulses are described as modulated pacing pulses. Thus, if the data is encoded on pacing pulses then supra-threshold pulses are used.

Other typical communication schemes used for data communication by a telemetry unit involve either RF or magnetic communication. RF frequencies of ~400 or ~900 MHz or magnetic coupling in the 100s of kHz range generally require several mA of current to transmit and receive data. Such high current requirements are typically out of reach of devices with battery capacities of at most a few hundred mAh.

In addition, typical RF schemes require large antennas and magnetic coupling requires large transmit and receive coils for communication. Generally, the space available in an iLP (intracardiac leadless pacer), for instance, would not allow such large coils or antennas. iLPs are often designed to be placed within a heart chamber as opposite to conventional pacemakers, where the pacemaker itself is placed outside the heart and electrode leads extend from the pacemaker into the heart.

U.S. Pat. No. 6,704,602 to Berg et al., entitled "Implanted Medical Device/External Medical Instrument Communication Utilizing Surface Electrodes", discloses a medical device communication system using sub-threshold pulses for electrical communication with external devices. The medical device communication system of Berg et al. includes an implantable medical device and external devices. The external devices may be connected to the skin of a body with a plurality of electrodes. The implantable medical device includes stimulation electrodes, surface electrodes in contact with tissue of a patient, and a can including a pulse generation circuit. The reference also discloses an electrode switching circuit coupled to the pulse generation circuit and serves to deliver electrical stimulation pulses to the stimulation electrodes as therapy to a patient. Furthermore, Berg et al. discloses wherein the electrode switching circuit also serves to deliver subthreshold pulses to the surface electrodes of the can in a predetermined pattern of modulations constituting an encoded data signal that propagates as a signal transmission through the patient tissue. According to Berg et al., the plurality of electrodes connected to the external device serve to receive the sub-threshold pulses and allow the external device to detect the encoded data signal.

For example, United States Patent Publication 2012/0109236 to Jacobson et al., entitled "Leadless Cardiac Pacemaker With Conducted Communication", discloses a system for pacing a heart of a human including a leadless pacemaker in a hermetic housing with at least two electrodes and at least one external device with at least two skin electrodes. The electrodes of Jacobson et al. appear to deliver energy to stimulate a heart and to transfer information to or from the skin electrodes of the external devices. The information in Jacobson et al. is preferably encoded in sub-threshold pulses delivered by the electrodes and generated by a pulse generator in the housing of the leadless pacemaker. According to Jacobson et al., the hermetic housing of the leadless pacemaker may further comprise a controller configured to communicate with the external devices by transferring information through the electrodes. Jacobson et al. also discloses wherein the controller may be configured to communicate with the external devices outside of a refractory period or pacing pulse.

In view of the above, there is a need for a communication scheme with an implantable device that does not employ RF or magnetic coupling.

BRIEF SUMMARY OF THE INVENTION

One or more embodiments of the invention are related to an alternative implantable stimulation device and an alternative data communication system and method that minimizes battery drain from the implantable stimulation device's battery.

At least one embodiment of the invention may include an implantable stimulation device, which includes at least one stimulation module and at least one data communication module. In one or more embodiments, the at least one stimulation module may include or may be connected to at least two electrodes that may allow delivery of stimulation pulses. By way of at least one embodiment, the at least one stimulation module may include one or more of:
  a voltage source that may be connected to the at least two electrodes via at least one stimulation-pulse-switch that may control delivery of a pacing pulse,
  a DC-blocking capacitor that may be connected in series with the voltage source and one of the at least two electrodes, and
  an autoshort switch that may allow discharging of the DC-blocking capacitor via the at least two electrodes when the autoshort switch is closed.

According to one or more embodiments, the at least one data communication module may include at least one data transmission control module that may be connected to the autoshort switch and/or to the stimulation-pulse-switch. In at least one embodiment, the at least one data transmission control module may alternatingly open and close the autoshort switch during an autoshort period following the delivery of a stimulation pulse to thus modulate a autoshort pulse. In at least one embodiment, the at least one data transmission control module may alternatingly open and close the at least one stimulation-pulse-switch during the delivery of a stimulation pulse or during a stimulation pulse period to thus modulate a stimulation pulse.

In one or more embodiments the voltage source may include a capacitor that may be charged prior to delivery of a stimulation pulse for pacing a human heart. A blocking capacitor, in at least one embodiment, may be provided to block delivery of DC-voltage to the tissue to be stimulated.

One or more embodiments of the invention may allow an implantable stimulation device with limited battery supply the ability to transmit increased amount of data while using reduced power. In at least one embodiment, data transmission may be achieved by modulating a local electric field generated by the implantable stimulation device and read by the receiver. Continuous medium rate data transmission, in at least one embodiment, may be achieved while using reduced battery power.

By way of one or more embodiments, the at least one data communication module may sense an oscillatory electric field imposed on body tissue surrounding the implantable stimulation device when the implantable stimulation device is in its implanted state. Thus, in at least one embodiment, it is possible to synchronize switching of the autoshort switch and/or the stimulation-pulse-switch with the oscillatory electric field imposed on the body tissue surrounding or encompassing the implantable stimulation device. The synchronization may be phase synchronized. In one or more embodiments, data communication of the implantable medical device is activated upon sensing an oscillatory electric field.

To implement synchronizing, according to one or more embodiments of the invention, the data communication module may include a phase-locked loop (PLL) and a frequency divider, wherein the PLL may lock in a frequency of an oscillatory electric field imposed on body tissue surrounding the implantable stimulation device when the implantable stimulation device is in its implanted state. The frequency divider, in at least one embodiment, may be connected to the PLL and may divide a frequency signal put out by the PLL. Thus, in one or more embodiments of the invention, the implantable stimulation device may generate a code that may represent data to be transmitted from the implantable stimulation device to an external device. In one or more embodiments, a clock for such code may be provided and may be a fraction of the frequency of the oscillatory electric field imposed on the body tissue surrounding the implantable stimulation device. The clock frequency, in at least one embodiment, may be in a range of 0.1 to 50 kHz, such as a range of 1 to 20 kHz, more preferably in a range of 7 to 9 kHz, and most preferably the clock frequency is 8 kHz.

According to at least one embodiment, the data communication module may be connected to the at least two electrodes and may sense an oscillatory electric field imposed on body tissue via the at least two electrodes. The data communication module, in at least one embodiment, may include a band-pass filter, wherein the band-pass filter may filter a signal fed to the phase-locked loop.

One or more embodiments of the invention may include a data communication system including an implantable stimulation device as described above and an external device that may include or may be connected to at least two cutaneous electrodes. The external device, in at least one embodiment, may include at least one external field generating module that may generate an oscillatory electric field to be transcutaneously imposed on the body via the at least two cutaneous electrodes. In one or more embodiments, the external device may include at least one sensor module that may sense alterations of body impedance and/or a local electric field generated by the implantable stimulation device when the implantable stimulation device is in its implanted state.

By way of one or more embodiments, the external device may include one or more of a lock-in amplifier, an AM demodulator that may demodulate amplitude-modulated signals, and an analog-to-digital converter, wherein the analog-to-digital converter may be connected to the AM demodulator and the lock-in amplifier, and wherein the analog-to-digital converter may put out a signal that represents a signal transmitted by the implantable stimulation device.

In at least one embodiment of the invention, the implantable device may include a hermetically sealed housing. The hermetically sealed implantable device with a hermetically sealed housing, in at least one embodiment, may be a medical therapy and/or a monitoring device.

According to one or more embodiments of the invention, a method of communicating data from an implantable stimulation device to an external device may be provided, wherein the method may include one or more of:

altering a local electric field in the body using the implantable stimulation device, by modulating an autoshort pulse or a stimulation pulse amplitude that may be delivered by the implantable stimulation device, and, sensing the change of the local electric field caused by the modulation of the autoshort pulse and/or a stimulation pulse amplitude, respectively, using an external device that includes or may be connected to at least two cutaneous electrodes.

Additionally, in at least one embodiment, the method may include, before the step of altering a local electric field, one or more of the steps of:

imposing an oscillatory electric field in body tissue encompassing an implantable stimulation device using an external device comprising at least two cutaneous electrodes, and, sensing the imposed oscillatory electric field using the implantable stimulation device.

In one or more embodiments, the step of altering the local electric field using the implantable stimulation device may be performed using at least two electrodes that may be connected to, operatively connected to, or may be part of the implantable stimulation device, and at least one data transmission control module that may be connected to, or operatively connected to, the at least two electrodes. In at least one embodiment, the at least one data transmission control module may be controlled to modulate a stimulation pulse amplitude and/or an autoshort pulse to a code-representing data that may be transmitted from the implantable stimulation device to the external device. In at least one embodiment, the modulating may cause a detectable change of a local electric field.

Preferably, in one or more embodiments, the modulation of a stimulation pulse amplitude may include amplitude changes without return to a baseline amplitude.

According to at least one embodiment of the invention, a transceiver may be utilized that may impart an electric field across the implantable stimulation device. At least one embodiment of the invention may include a lock-in amplifier that may detect changes in the local field around the implantable device, and an implantable device that may use charge to alter the local electric field.

During an autoshort period following delivery of a stimulation pulse, by way of one or more embodiments, the implantable device may use the residual charge from the pacing pulse and may modulate the balancing of such charge to effect communication. In this case, in at least one embodiment, the residual charges may form the local electric field that may be altered to effect communication. In at least one embodiment, if communication may be required during the delivery of a stimulation pulse, fast modulation of the stimulation-pulse peak amplitude without return to baseline may effect communication instead. In this case, in one or more embodiments, the stimulation pulse may form the local electric field that may be altered to effect communication.

According to one or more embodiments, amplifying the local impedance or electric field change around the implantable stimulation device may increase the signal-to-noise ratio and may make communication more reliable. Also, in at least one embodiment, allowing communication while pacing may increase the allowable communication time for data communication.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
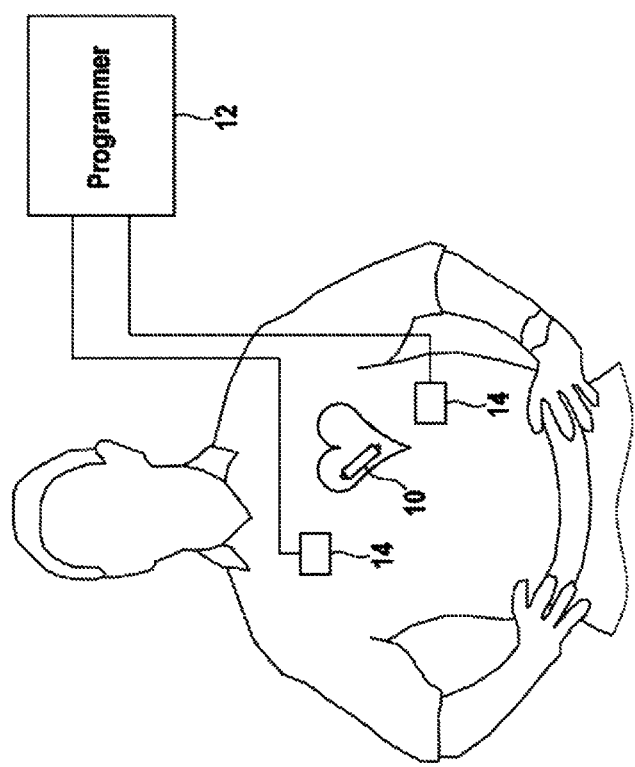
FIG. 1: is a representation of a communication system, including an implantable stimulation device in its implanted state and an external device, according to at least one embodiment of the invention.

FIG. 1 shows a representation of a communication system, including an implantable stimulation device in its implanted state and an external device, according to at least one embodiment of the invention. As shown in FIG. 1, at least one embodiment of the invention includes an implantable pacemaker such as an implantable stimulation device 10, a programmer/communication device such as external device 12, and at least two cutaneous electrodes 14 placed on either side of the heart. In at least one embodiment, the external device 12 may detect changes of a local electric field in the body. In particular, in one or more embodiments, the external device 12 may detect changes of a local electric field in the body caused by a stimulation pulse and/or autoshort pulse. The external device 12, in at least one embodiment, may induce an oscillating electric field through the at least two cutaneous electrodes 14 between 50 kHz to 1 MHz, preferably between 300 to 500 kHz, at a specific voltage or current. In at least one embodiment, the stimulation device 10 implanted in the heart may be located between the at least two cutaneous electrodes 14; as shown in FIG. 2.

Figure 2:
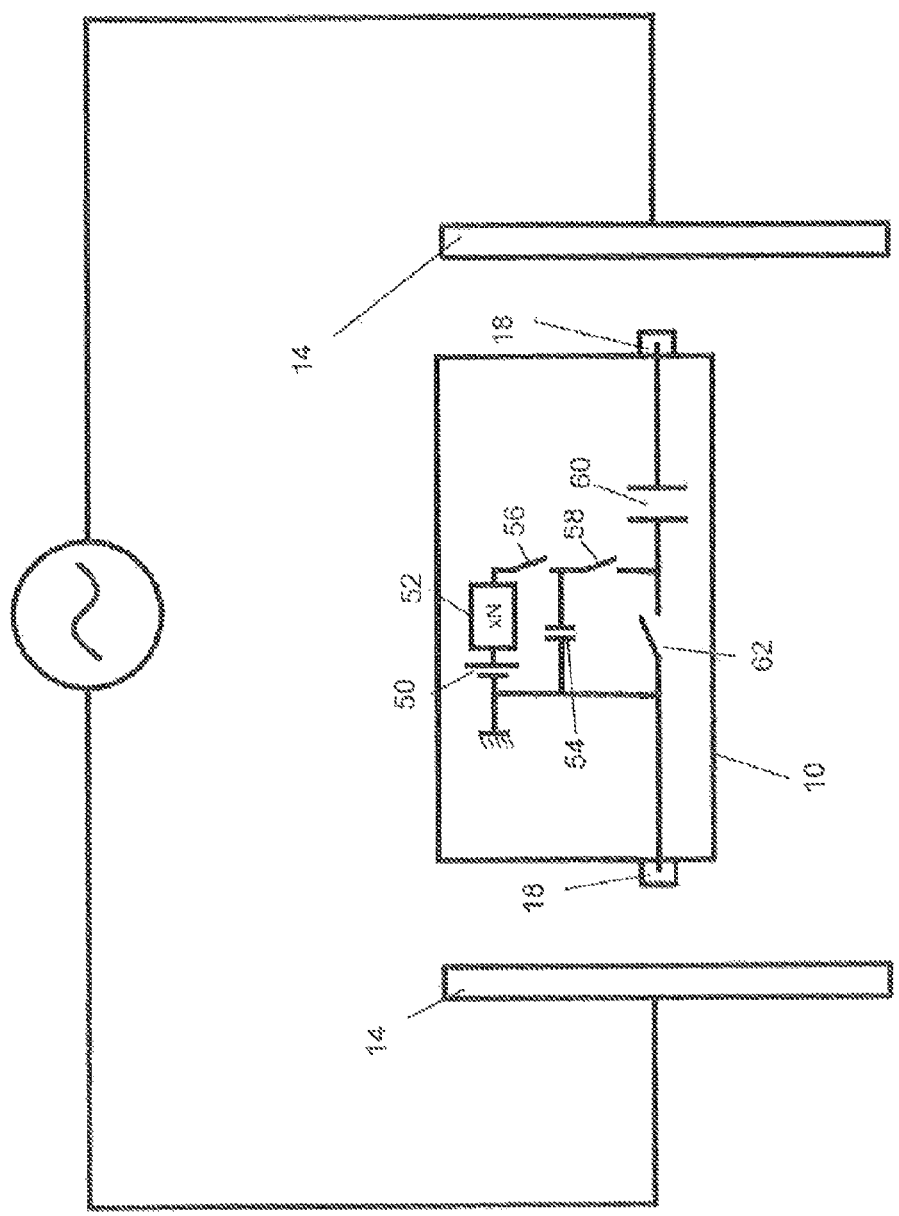
FIG. 2: is a more abstract representation of the system depicted in FIG. 1, according to at least one embodiment of the invention.

FIG. 2 is a more abstract representation of the system depicted in FIG. 1, according to at least one embodiment of the invention. In one or more embodiments, the implantable stimulation device 10 includes a battery 50 with limited capacity. Optionally, in at least one embodiment, to multiply the voltage $V_{bat}$ of battery 50 to generate a voltage needed for a stimulation pulse, a voltage multiplier 52 may be provided. By way of at least one embodiment, a stimulation pulse capacitor 54 may be provided that may be charged when connected to voltage multiplier 52 or battery 50. To enable charging of the stimulation pulse capacitor 54, in one or more embodiments, a charging control switch 56 may be provided. In at least one embodiment, the stimulation pulse capacitor 54 may be charged when charging control switch 56 may be closed.

According to one or more embodiments of the invention, to deliver the charge from stimulation pulse capacitor 54 to electrodes 18 and to thus deliver a stimulation pulse, a stimulation-pulse-switch 58 may be provided. In at least one embodiment, when the charging control switch 56 is opened and the stimulation-pulse-switch 58 is closed, current may flow to electrodes 18 via a blocking capacitor $C_{block}$ 60. Via stimulation-pulse-switch 58, in one or more embodiments, the duration of a stimulation pulse period may be controlled. In at least one embodiment, the stimulation pulse period may last as long as stimulation-pulse-switch 58 is closed.

By way of one or more embodiments, after delivery of a stimulation pulse when the stimulation-pulse-switch 58 is opened, charge remaining on blocking capacitor 60 may be discharged via autoshort switch 62 and electrodes 18. Thus, in at least one embodiment, an autoshort pulse may be generated that may dissipate charge on the blocking capacitor remaining from the stimulation pulse. As such, in one or more embodiments, the autoshort pulse may be controlled by autoshort switch 62.

According to at least one embodiment, autoshort switch 62 may be controlled by at least one data communication module (not shown in FIG. 2). According to at least one embodiment, at least one data communication module may comprise at least one data transmission control module that may control autoshort switch 62.

By way of one or more embodiments, utilizing the charge present on the blocking capacitor 60 after delivery of a stimulation pulse may effect an observable change of an electric field that may be used for data transmission. Often, after delivery of a stimulation pulse, the residual charge on the blocking capacitor 60 may be removed by shorting the stimulation electrodes 18 together (autoshort). The voltage left on the capacitor 60 after delivery of a stimulation pulse, for example, may not be stimulating voltage, rather, it is unused. As such, it is a by-product of pacing and detrimental to leads and tissue. Therefore, in at least one embodiment, it may be removed to prevent for example electrode corrosion and therefore autoshort switch 62 may be provided. By modulating the shorting process to encode data, in at least one embodiment, a detectable data transmission signal may be produced. In at least one embodiment, the modulation may include any suitable modulation and coding, for example amplitude modulation (AM) or amplitude modulation that is binary phase shift keying encoded (AM-BPSK).

By way of one or more embodiments, the modulated residual charge may create a large change in the local field around the implantable stimulation device 10 that may cause large voltage changes as sensed by the external device 12. The external device 12, in at least one embodiment, may impart an oscillatory electric field on the body that may create a carrier for the implanted device to use for transmission. In one or more embodiments, the implantable medical device activates data communication upon sensing an oscillatory electric field. In one or more embodiments, modulating the charge present after delivery of a stimulation pulse may cause the local field to change within the frequency range of a receiving lock-in amplifier of the external device 12. A synchronization of the modulation to the frequency of the externally imparted electric field, in at least one embodiment, may improve signal-to-noise ratio. In at least one embodiment, the change in the field produced by the external device 12, which includes a receiver, may cause communication. This communication, in one or more embodiments, may be termed pseudo-passive because charge may be used to change the local field, whereas passive may only use a switch.

Figure 6:
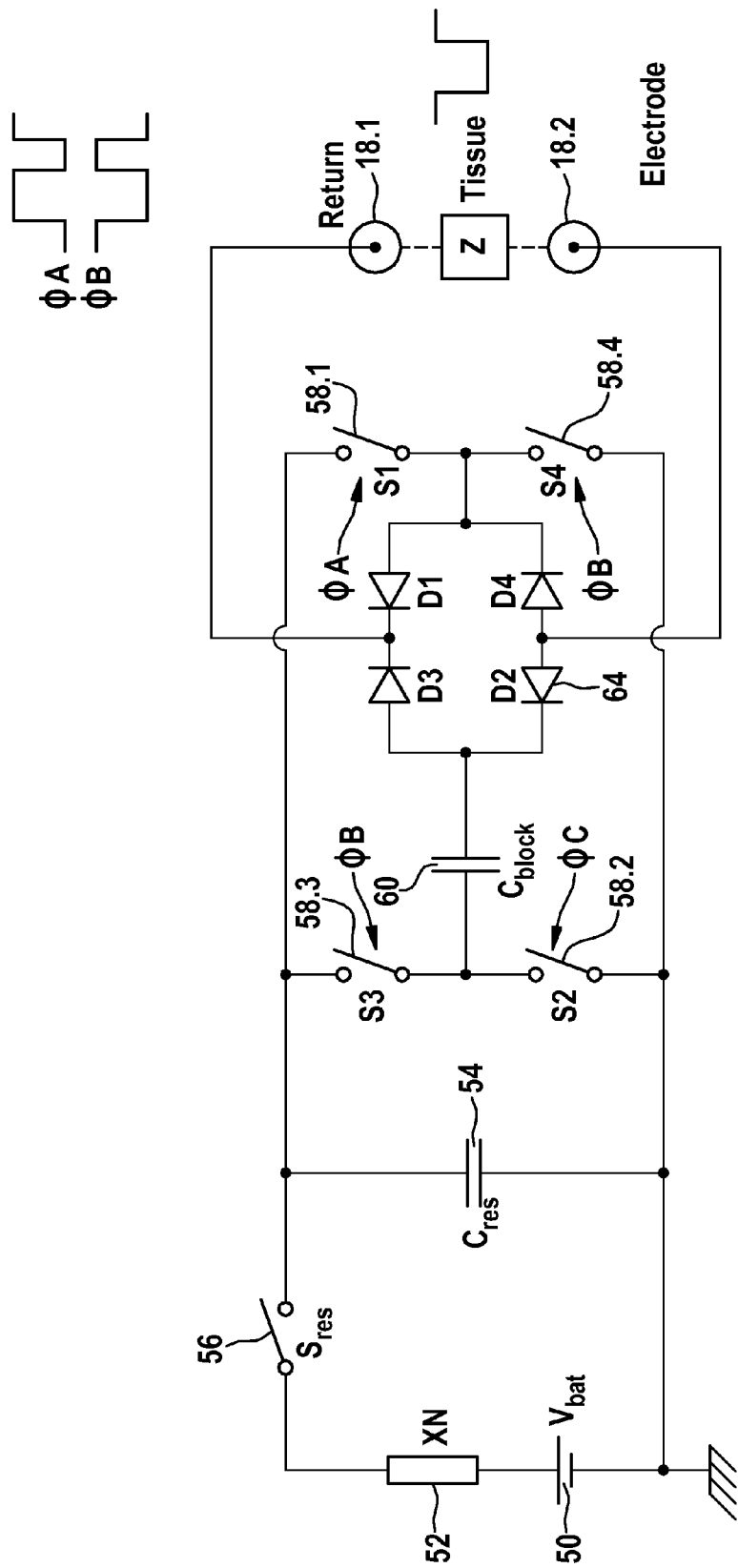
FIG. 6: is a schematic representation of a pacing circuit for data transmission during a stimulation pulse, according to at least one embodiment of the invention.

In at least one embodiment, this method may be extended for use with stimulation pulses. Fast modulation of stimulation-pulse peak amplitudes, without return to baseline, in one or more embodiments, may be achieved using a circuit that may include one or more of a blocking capacitor $C_{block}$ 60, a rectifier diode bridge 64, and four switches 58.1, 58.2, 58.3 and 58.4, as shown in FIG. 6 and discussed further below. In at least one embodiment, one or more of the switches 58.1, 58.2, 58.3 and 58.4 may allow bi-directional current flow through the blocking capacitor $C_{block}$ 60, and such current may be unidirectionally delivered to tissue via the rectifier diode bridge 64. The blocking capacitor $C_{block}$ 60, in one or more embodiments, may charge and discharge within the delivery of a stimulation pulse and may be sized to provide the desired modulation of the peak amplitude of the stimulation pulse. This approach, in at least one embodiment, may result in a smaller blocking capacitor $C_{block}$ 60 which may be an advantage for volume-constrained applications such an iLP. In at least one embodiment modulation of stimulation pulse amplitude is controlled such, that an average peak amplitude is maintained.

Figure 4:
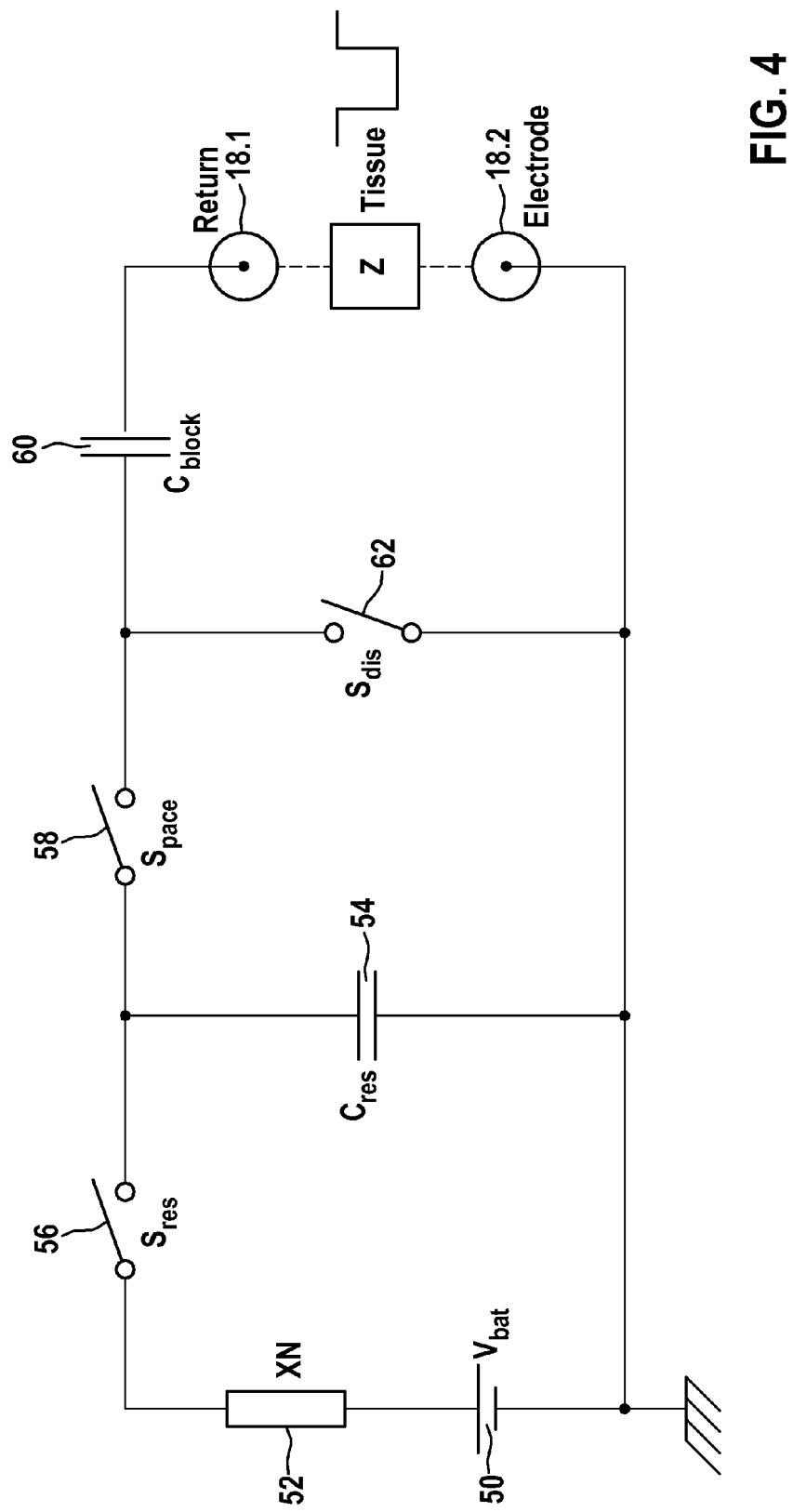
FIG. 4: is a schematic representation of a pacing circuit for data transmission during the autoshort period, according to at least one embodiment of the invention.

According to one or more embodiments, passive charge balancing of a pacing pulse may involve the connection of on or more analog switches that may allow discharging of the blocking capacitor $C_{block}$ 60 through tissue, returning charge for neutrality purposes. FIG. 4 shows a schematic representation of a pacing circuit for data transmission during the autoshort period, according to at least one embodiment of the invention. In such a circuit, in at least one embodiment, capacitor $C_{res}$ 54 may be charged via switch $S_{res}$ 56 to a multiple N of the battery voltage $V_{bat}$ 50 (N can be 1). In at least one embodiment, AC-coupled stimulation, via capacitor $C_{block}$ 60, may occur by opening switch $S_{res}$ 56 and closing switch $S_{pace}$ 58, connecting capacitor $C_{res}$ 54 in series with $C_{block}$ 60 and tissue (represented by Z) between electrodes 18. In one or more embodiments, capacitor $C_{block}$ 60 may then charge during the delivery of the stimulation pulse and such charge may flow in the opposite direction following the stimulation pulse (opening of switch $S_{pace}$ 58) to allow for charge-balanced stimulation. In at least one embodiment, this may be achieved by closing switch $S_{dis}$ 62 for a finite time that may depend on the $Re(Z) \times C_{block}$ time constant.

By way of one or more embodiments, fast connection/disconnection of switch $S_{dis}$ 62 causes interruption of the balancing autoshort pulse, which in turn creates voltage glitches between the electrodes 18. Such glitches, in at least one embodiment, may be detected using a lock-in amplifier, as disclosed in FIG. 8 and discussed further below.

Figure 3:
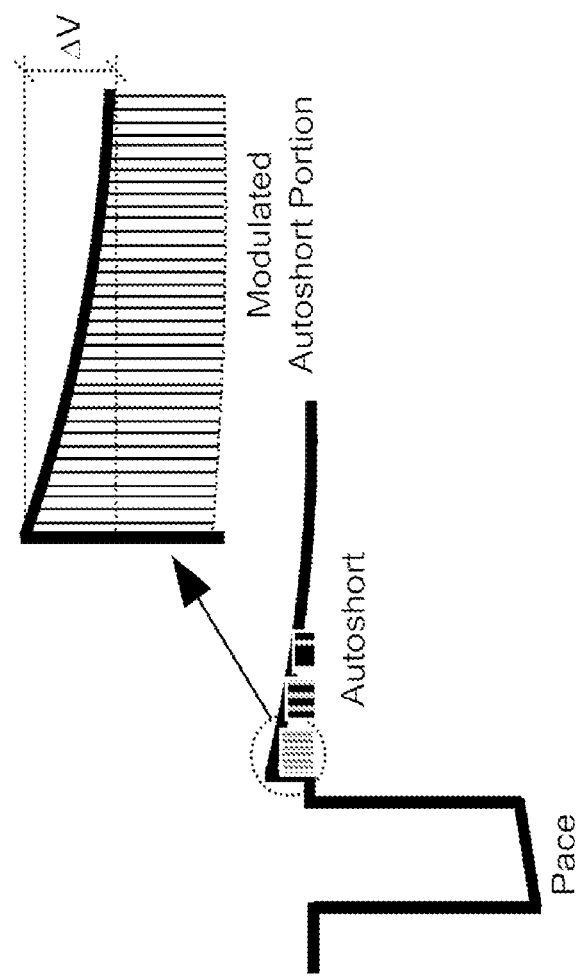
FIG. 3: is a stimulation pulse showing modulation of the autoshort period, according to at least one embodiment of the invention.

FIG. 3 illustrates a stimulation pulse showing modulation of the autoshort period, according to at least one embodiment of the invention. As shown in FIG. 3, in at least one embodiment, transmission during the balancing phase may be divided into different sections. In one or more embodiments, each section may be selected according to a maximum ΔV discharge of the blocking capacitor that may allow decoding the glitches within a section using the same integration time for the receiving lock-in amplifier. Consecutive transmission sections, in at least one embodiment, may have increasing integration times until charge balancing completes. In at least one embodiment, transition from one section to the next may be achieved by simple start and stop bits in the link layer.

According to one or more embodiments, the implantable stimulation device 10 may measure the lead impedance and may compare such value against those in a non-volatile table stored in the device's memory to support determination of each section's modulating frequency. In at least one embodiment, this information may be transmitted to the external receiver during synchronization, or extracted by such, to determine the corresponding integration times that may be used.

Figure 5:
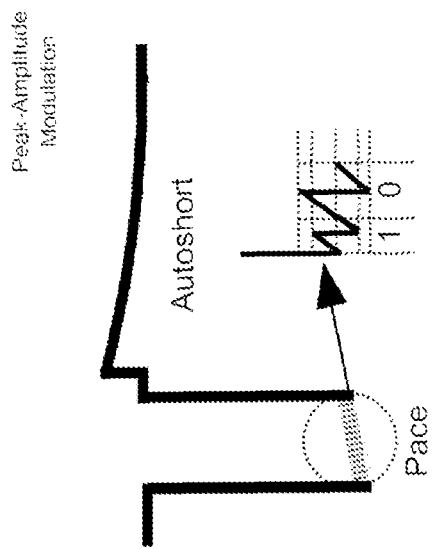
FIG. 5: is a stimulation pulse showing modulation of the peak amplitude without return to baseline, according to at least one embodiment of the invention.

FIG. 5 is a stimulation pulse showing modulation of the peak amplitude without return to baseline, according to at least one embodiment of the invention. According to at least one embodiment, FIG. 5 shows modulation of the stimulation-pulse peak amplitude instead, for data transmission during delivery of a stimulation pulse. Such modulation, in at least one embodiment, may be achieved with the circuit shown in FIG. 6.

FIG. 6 is a schematic representation of a pacing circuit for data transmission during a stimulation pulse, according to at least one embodiment of the invention. As shown in FIG. 6, similar to the circuit diagram shown in FIG. 4, capacitor $C_{res}$ 54 may be charged to a multiple N of the battery voltage $V_{bat}$. To cause delivery of a stimulation pulse, in at least one embodiment, switch $S_{res}$ 56 may be opened and switches 58.1, 58.2, 58.3 and 58.4 may be opened and closed in an H-bridge type of configuration. For example, in one or more embodiments, during the high-phase of $\Phi_A$, switches 58.1 and 58.2 may be closed simultaneously which may allow diodes D1 and D2 to conduct flowing current from the first electrode 18.1 to the second electrode 18.2. In one or more embodiments, $C_{block}$ may then charge in the direction of diode D2 and switch 58.2, reducing (approximately linearly) the voltage across Z. The former, in at least one embodiment, may be dimensioned to provide the desired amplitude/timing modulation shown in FIG. 5 (for a range of Re(Z)).

According to one or more embodiments, in the opposite phase, i.e. high $\Phi_B$ and low $\Phi_A$, switches 58.1 and 58.2 may be opened and switches 58.3 and 58.4 may be closed. The accumulated voltage on $C_{block}$ 60, in at least one embodiment, will instantaneously add to the stimulation pulse peak voltage, making the transitions shown in the zoom of FIG. 5. In at least one embodiment, current flows through switch 58.3 to capacitor $C_{block}$ 60 to diode D3 to diode D4 to switch 58.4, thus discharging $C_{block}$ 60.

In at least one embodiment, diodes D1, D2, D3 and D4 shown in FIG. 6 may be replaced by switching elements for high efficiency implementation.

In one or more embodiments, combination of the schematized circuits of FIG. 4 and FIG. 6 may be provided to achieve data transmission during both the stimulation pulse period and the autoshort period.

Figure 7:
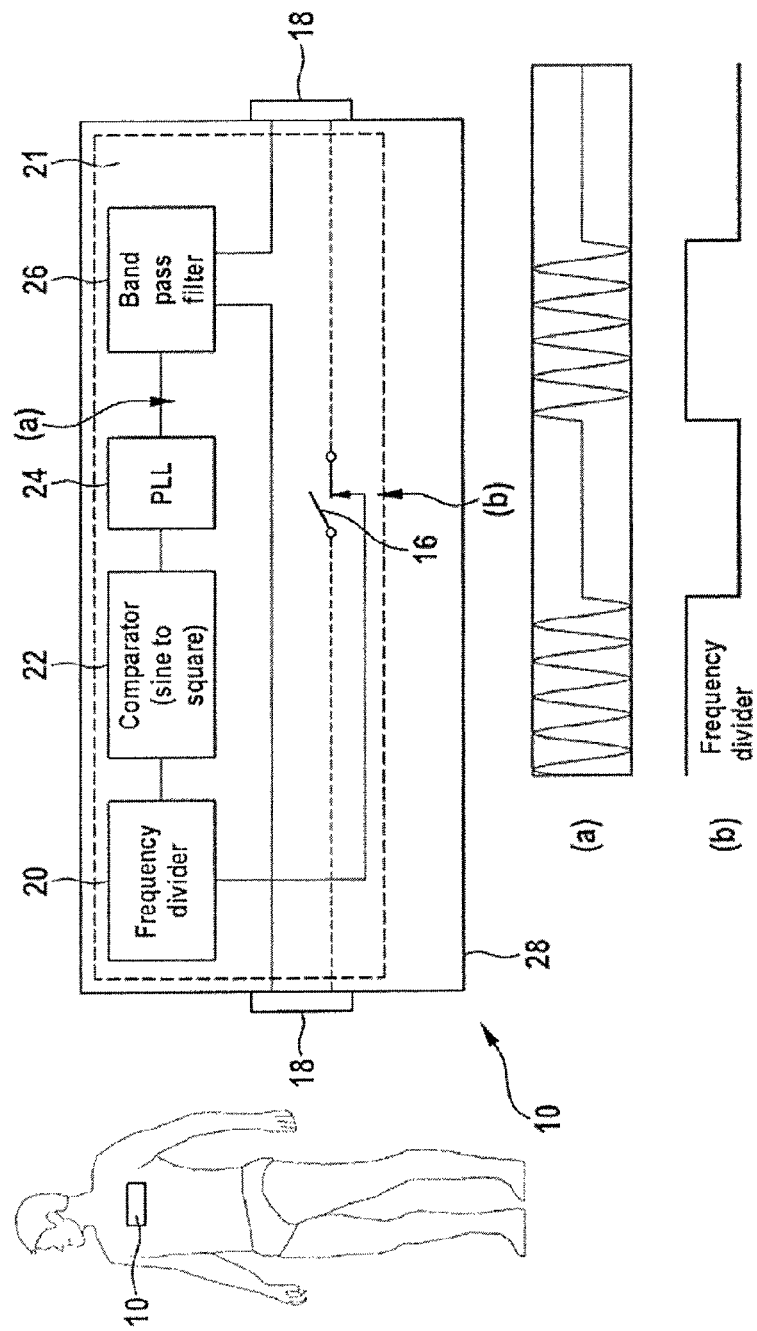
FIG. 7: is a representation of an embodiment of an implantable stimulation device showing elements that allow synchronization of the switching with an imposed oscillatory electric field, according to at least one embodiment of the invention.

FIG. 7 is a representation of an embodiment of an implantable stimulation device showing elements that allow synchronization of the switching with an imposed oscillatory electric field, according to at least one embodiment of the invention. As shown in FIG. 7, the implantable stimulation device 10 may include at least two electrodes 18 that may contact body tissue surrounding the implantable stimulation device 10 in its implanted state, wherein the at least two electrodes 18 may be implantable electrodes. By way of at least one embodiment, switch 62 and switches 58.1, 58.2, 58.3 and 58.4, respectively, may be represented by single switch 16 as shown in FIG. 7.

In one or more embodiments, the at least two electrodes 18 of the implantable stimulation device 10 may be arranged on the external surface of a hermetically sealed housing 28 encapsulating the implantable stimulation device 10. According to at least one embodiment, parts of the housing 28 itself may form the at least two electrodes 18. In one or more embodiments, the at least two electrodes 18 may also be formed by a tip electrode 18 that may be located at a tip of the implantable stimulation device 10, and a ring electrode that may be located on the circumference of the implantable stimulation device 10 (not shown).

In order to control switching of the switch or switches represented by switch 16, in at least one embodiment, the implantable stimulation device 10 may include a frequency divider 20 that may be connected to a sine-to-square converting comparator 22 that in turn may be connected to a phase-locked loop (PLL) 24. In one or more embodiments, phase-locked loop 24 may be connected to the at least two electrodes 18 via a band-pass filter 26. In at least one embodiment, phase-locked loop 24 and frequency divider 20 may be part of a switch control of implantable stimulation device 10.

In one or more embodiments, the field induced between the cutaneous electrodes 14 may be sensed by the implantable stimulation device 10. In at least one embodiment, the implantable stimulation device 10 may lock in the frequency of the electric field using the phase-locked loop 24. Once the implantable stimulation device 10 may be locked on to the frequency of the external device's induced field, in one or more embodiments, it may activate the switch 16 between the at least two electrodes 18 that may be in the field in synch with the frequency of the electric field, as shown in FIG. 2 and FIG. 4.

In at least one embodiment of the invention, the implantable stimulation device 10 may receive the imposed oscillatory electric signal as input signal that may be detected via the at least two electrodes 18. Thus, in one or more embodiments, the implantable stimulation device 10 may have an input sine signal that may be detected as an alternating voltage across electrodes 18 or across a resistor. This input sine signal, in one or more embodiments, may be band-pass filtered by band-pass filter 26. A representation of such a band-pass filtered signal is shown in representation (a) of FIG. 7.

In at least one embodiment, the band-pass filtered input sine signal is fed to the phase-locked loop (PLL) 24 that locks in the frequency of the input sine signal. PLL 24, in one or more embodiments, may put out a synchronized sine signal to a comparator 22 that may convert the sine signal, depicted by representation (a) of FIG. 7, to a square signal depicted by representation (b) of FIG. 7. The square signal thus generated, in at least one embodiment, may be fed to frequency divider 20 that may generate a clock signal for switching the switch

16. In one or more embodiments, the clock signal thus generated may have a frequency corresponding to a fraction of the frequency of the oscillatory electric field wherein the fraction may be determined by a frequency division factor applied by frequency divider 20. The clock signal frequency, in at least one embodiment, may be in a range of 0.1 to 50 kHz, such as a range of 1 to 20 kHz, more preferably in a range of 7 to 9 kHz, most preferably the clock signal frequency is 8 kHz.

According to one or more embodiments, the actual switching of the switch or switches represented by switch 16 may further depend on data that may be transmitted from the implantable stimulation device 10 to the external device 12. The data to be transmitted, in at least one embodiment, may be coded and the code may determine the actual sequence of switching of the switch or switches represented by switch 16.

In at least one embodiment, frequency divider 20 may be a flip-flop counter.

In one or more embodiments, the change of an electrical field caused by switching the switch 62 and/or switches 58.1, 58.2, 58.3 and 58.4 represented by switch 16 may be sensed by external device 12.

In at least one embodiment of the invention, data transmission from the implantable stimulation device 10 to the external device 12 may be summarized as follows: generate a local electric field in the body by discharging a capacitor to the body tissue, switch on/off the switch or switches represented by switch 16 in implantable device 10 to cause changes of the body electric field and detect change by external device 12.

In at least one embodiment of the invention, data transmission from the implantable stimulation device 10 to the external device 12 may be summarized as follows: apply signal (oscillatory electric field), propagate in body, switch on/off the switch or switches represented by switch 16 in implantable device 10 to cause changes of the body electric field and detect change by external device 12.

In one or more embodiments, the switch control of the implantable stimulation device 10 may receive an input sine signal by detecting a voltage across electrodes 18. The switch control of the implantable stimulation device 10, according to at least one embodiment of the invention, may include one or more of a band-pass filter 26, a phase-locked loop 24 that may lock in the frequency of the input sine signal, a comparator 22 that may convert the sine signal to a square signal, and a flip-flop counter that may act as a frequency divider 20 that may control the at least one switch 16. Switch 16, in at least one embodiment, may have a small on-resistance.

Figure 8:
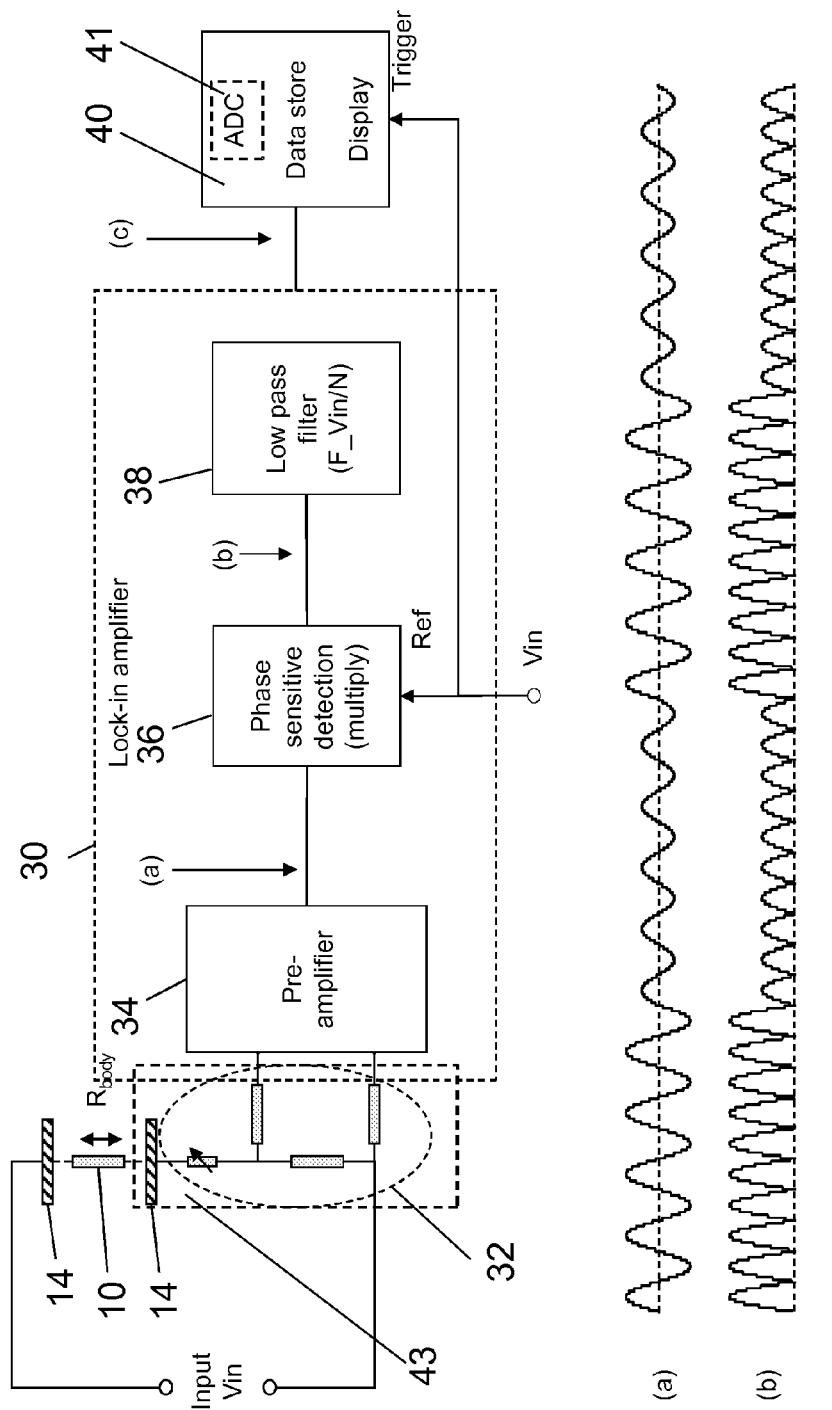
FIG. 8: is a more detailed representation of an external device showing those elements, according to at least one embodiment of the invention.

In one or more embodiments, the changes of the electric field caused by the implantable stimulation device 10, as shown in FIG. 4 and FIG. 6, may be detected by the external device 12. FIG. 8 is a more detailed representation of an external device showing those elements, according to at least one embodiment of the invention. As shown in FIG. 8, the external device 12 may include a lock-in amplifier 30 that may generate an output signal (depicted as representation (c) of FIG. 8) that may represent the signal that may be transmitted by implantable stimulation device 10 by way of electric field changes. Lock-in amplifier 30, in at least one embodiment, may use the signal imposed on a body by means of cutaneous electrodes 14 as a reference signal. For this purpose, in at least one embodiment, a network of resistors 32 may be provided that may cause a voltage drop representing the signal (the oscillatory electric field) imposed on a body via cutaneous electrodes 14.

In one or more embodiments, this signal may be amplified by pre-amplifier 34 of lock-in amplifier 30.

By way of one or more embodiments, the amplified signal sensed via at least one sensing module 43, i.e. at least two cutaneous electrodes 14 and the resistor network 32, may be fed to an AM demodulator that may include a phase-sensitive detector 36, and may further be fed to a low-pass filter 38, as depicted in FIG. 8. The amplified input signal sensed via cutaneous electrodes 14 and the resistor network 32, in at least one embodiment, may be represented as signal (a) of FIG. 8. The output signal of the phase-sensitive detector 36, in at least one embodiment, may be depicted as signal (b) of FIG. 8. In one or more embodiments, the low-pass filtered output signal of lock-in amplifier 30 may be depicted in FIG. 8 as signal (c). In at least one embodiment, signal (c) may correspond to the signal generated by implantable stimulation device 10 and may represent data to be transmitted from implantable stimulation device 10 to external device 12. In at least one embodiment, this signal may be analog-to-digital converted and stored. In one or more embodiments, block 40 in FIG. 8 may include one or more of an analog-to-digital converter (ADC) 41, a memory for data storage and a display of external device 12.

According to at least one embodiment, for the detection of electric field changes of the body caused by the implantable stimulation device 10, the external device 12 may include a lock-in amplifier 30 that may use the input as a reference signal, including an AM demodulator which in turn may include a precision rectifier and a low-pass filter 38. The low-pass filtered signal, in at least one embodiment, may be fed to an analog-to-digital converter 41.

In one or more embodiments, the communication from implantable stimulation device 10 to external device 12 may be understood as follows.

In at least one embodiment, as the implantable stimulation device 10 alternatively shorts and opens the switch 62 or switches 58.1, 58.2, 58.3 and 58.4 represented by switch 16, the electric field between the external device electrodes 14 may be slightly changed or modulated. In one or more embodiments, the external device 12 may sense the change of the electric field by measuring how much voltage or current may be imparted on the electrodes 14 that may create the oscillator electric field between the external device electrodes 14.

In at least one embodiment, the external device 12 may implement detection using a lock-in amplifier 30 that may be synchronized to the electric field frequency and phase. As the implantable stimulation device 10 modulates the electric field between the external device electrodes 14, in one or more embodiments, the external device 12 may integrate the changing current or voltage. In at least one embodiment, the integration may allow a very small change in sourced voltage or current that may be detected using amplitude modulation.

In one or more embodiments, communication may occur at approximately $1/10$ to $1/100$th of the modulation frequency of the imposed oscillatory electric field. In at least one embodiment, this may allow for ~10-100 cycles of the electric field to be integrated that may determine the imparted current or voltage.

By way of one or more embodiments, a communication from external device 12 to implantable stimulation device 10 may be done as follows:

In at least one embodiment, the imposed oscillatory electric field may include a fundamental frequency that the implantable stimulation device 10 may use to lock onto. The fundamental frequency, in one or more embodiments, may also be used as a carrier frequency to send modulated data to the implantable stimulation device 10. According to at least one embodiment, the external device 12 may modulate data, using frequency modulation or amplitude modulation, on top of the carrier imparted electric field. The implantable stimulation device 10, in at least one embodiment, may decode the modulated data sensed through the electrodes 18.

One or more embodiments of the invention may not require the implantable stimulation device 10 to actively transmit data using its own power in the case of impedance modulation embodiment. Rather, in at least one embodiment, the implantable stimulation device 10 may modulate a field imparted on it by an external device 12. In one or more embodiments, the resulting drain on the implantable stimulation device's battery may be negligible. Because of the reduced power consumption, in at least one embodiment, it may be possible to transmit more data to the external device 12.

In one or more embodiments, modulating a local electric field as described above may allow for improved data communication than data communication provided by causing pure impedance changes (passive). In at least one embodiment, the changes in the local electric field may produce much larger changes in the sensed voltage at the receiver than pure impedance changes between electrodes of the implantable device. Because of the large sensed difference, in at least one embodiment, a shortened integration time may be possible. In one or more embodiments, by shortening the integration time of the lock-in amplifier, higher data rates may be achieved.

Further, in at least one embodiment of the invention, utilizing this method may enable post-stimulation-pulse transmission of data.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable stimulation device comprising:
at least one stimulation module;
at least two electrodes configured to allow delivery of stimulation pulses; and,
at least one data communication module;
wherein said at least one stimulation module comprises a voltage source,
wherein said voltage source is configured to connect to the at least two electrodes via at least one stimulation-pulse-switch that is configured to control delivery of a pacing pulse,
at least one DC-blocking capacitor connected in series with the voltage source and the at least two electrodes, and
an autoshort switch configured to allow discharging of the at least one DC-blocking capacitor via the at least two electrodes when the autoshort switch is closed;
wherein said at least one data communication module comprises at least one data transmission control module connected to the autoshort switch and is configured to
alternatingly open and close the autoshort switch during an autoshort period following the delivery of a stimulation pulse to modulate a autoshort pulse amplitude,
wherein the at least one data communication module is connected to the at least two electrodes and is further configured to sense an oscillatory electric field imposed on body tissue surrounding the implantable stimulation device, and,
wherein the data communication module further comprises a phase-locked loop (PLL) and a frequency divider, wherein the phase-locked loop is configured to lock in a frequency of the oscillatory electric field imposed on body tissue surrounding the implantable stimulation device, and wherein the frequency divider is configured to connect to the phase-locked loop and divide a frequency signal put out by the phase-locked loop.

2. The implantable stimulation device according to claim 1, wherein the at least one data transmission control module is further configured to control switching of the autoshort switch phase-synchronized with the oscillatory electric field imposed on body tissue surrounding the implantable stimulation device.

3. The implantable stimulation device according to claim 1, wherein the data communication module further comprises a band-pass filter, wherein the band-pass filter is configured to filter a signal fed to the phase-locked loop.

4. An implantable stimulation device comprising:
at least one stimulation module;
at least two electrodes configured to allow delivery of stimulation pulses; and,
at least one data communication module;
wherein said at least one stimulation module comprises a voltage source,
wherein said voltage source is configured to connect to the at least two electrodes via at least one stimulation-pulse-switch that is configured to control delivery of a pacing pulse,
wherein said at least one data communication module comprises at least one data transmission control module connected to the at least one stimulation-pulse-switch, and is configured to
alternatingly open and close the at least one stimulation-pulse-switch during a stimulation pulse period to modulate at least a portion of a stimulation pulse amplitude,
wherein the at least one data communication module is connected to the at least two electrodes and is further configured to sense an oscillatory electric field imposed on body tissue surrounding the implantable stimulation device, and,
wherein the data communication module comprises a phase-locked loop (PLL) and a frequency divider, wherein the phase-locked loop is configured to lock in a frequency of the oscillatory electric field imposed on body tissue surrounding the implantable stimulation device, and wherein the frequency divider is configured to connect to the phase-locked loop and divide a frequency signal put out by the phase-locked loop.

5. The implantable stimulation device according to claim 4, wherein the data transmission control module is configured to maintain an average peak amplitude of the stimulation pulse.

6. The implantable stimulation device according to claim 4, wherein the at least one data transmission control module is further configured to control switching of the at least one stimulation-pulse-switch phase-synchronized with the oscillatory electric field imposed on body tissue surrounding the implantable stimulation device.

7. The implantable stimulation device according to claim 4, further comprising four switches and a rectifier bridge, wherein the four switches and the rectifier bridge are configured to allow bi-directional current flow to generate a stimulation pulse having a modulated peak amplitude that is unidirectionally delivered to tissue via the rectifier bridge.

8. The implantable stimulation device according to claim 4, wherein the data communication module further comprises a band-pass filter, wherein the band-pass filter is configured to filter a signal fed to the phase-locked loop.

9. A data communication system comprising:
   an implantable stimulation device comprising
      at least one stimulation module;
      at least two electrodes configured to allow delivery of stimulation pulses; and,
      at least one data communication module;
      wherein said at least one stimulation module comprises
         a voltage source,
            wherein said voltage source is configured to connect to the at least two electrodes via at least one stimulation-pulse-switch that is configured to control delivery of a pacing pulse,
         at least one DC-blocking capacitor connected in series with the voltage source and the at least two electrodes, and
         an autoshort switch configured to allow discharging of the at least one DC-blocking capacitor via the at least two electrodes when the autoshort switch is closed;
      wherein said at least one data communication module comprises at least one data transmission control module connected to the autoshort switch and is configured to
         alternatingly open and close the autoshort switch during an autoshort period following the delivery of a stimulation pulse to modulate an autoshort pulse amplitude; and,
   a external device comprising at least two cutaneous electrodes;
      wherein the external device further comprises at least one sensor module configured to sense one or more of alterations of body impedance and a local electric field generated by the implantable stimulation device.

10. The data communication system according to claim 9, wherein the external device further comprises a lock-in amplifier, an AM demodulator configured to demodulate amplitude-modulated signals, and an analog-to-digital converter;
   wherein the analog-to-digital converter is connected to the AM demodulator and the lock-in amplifier, and
   wherein the analog-to-digital converter is configured to put out a signal that represents a signal transmitted by the implantable stimulation device.

* * * * *